United States Patent [19]
Hodson

[11] Patent Number: 5,883,130
[45] Date of Patent: Mar. 16, 1999

[54] NG-MONOMETHYL-L-ARGININE HYDROCHLORIDE DERIVATIVES AND THEIR USE IN THE TREATMENT OF SEPTIC SHOCK

[75] Inventor: Harold Francis Hodson, Kent, Great Britain

[73] Assignee: Glaxo Wellcome Inc., Research Triangle Park, N.C.

[21] Appl. No.: 55,786

[22] Filed: Apr. 7, 1998

Related U.S. Application Data

[62] Division of Ser. No. 862,468, May 23, 1997, Pat. No. 5,767,312, which is a continuation of Ser. No. 461,163, Jun. 5, 1995, abandoned, which is a continuation of Ser. No. 374,636, Jan. 23, 1995, abandoned.

[30] Foreign Application Priority Data

Jul. 24, 1992 [GB] United Kingdom ............... 9215816.1
Jul. 23, 1993 [WO] WIPO ....................... PCTGB9301563

[51] Int. Cl.$^6$ ........................... A01N 37/10; C07C 241/00
[52] U.S. Cl. ............................................. 514/569; 562/560
[58] Field of Search ............................... 562/560; 514/569

[56] References Cited

U.S. PATENT DOCUMENTS 5,225,440  7/1993  London .................................... 514/535
5,374,651  12/1994  Kilbourn ................................. 514/400

FOREIGN PATENT DOCUMENTS

WO 91/04024  4/1991  WIPO .

OTHER PUBLICATIONS

Vogel "A Textbook of Practical Organic Chemistry" 3$^{rd}$ Ed., pp 122–136, 1956.
Kilbourn et al Proc. Natl. Acad. Sci. USA; vol. 87, pp. 3629–3632; May 1990 NG–Methyl–L–arginine inhibits tumor necrosis factor–induced hypotension: Implications for the involvement of nitric oxide.
European Search Report PCT/GB93/01563.
Prabhakaran et al J.Am. Chem. Soc. 1988, 110, 5785–5791 Biosynthesis of Blasticidin S from L–α–Arginine etc.
546C88 for Septic Shock –Study termination Apr. 24, 1998 London.
Scrip Display Apr. 27, 1998 Glaxo Wellcome hits problems in sepsis.

Primary Examiner—Gary Geist
Assistant Examiner—Brian J. Davis
Attorney, Agent, or Firm—Nixon & Vanderhye

[57] ABSTRACT

Crystalline $N^G$-monomethyl-L-arginine hydrochloride is disclosed. At least three distinguishable isomorphic forms are present. The solid salt can be made by dissolving $N^G$-monomethyl-L-arginine in hydrochloric acid and crystallising out $N^G$-monomethyl-L-arginine hydrochloride. The crystallising step requires several months at low temperature. However, the process can be facilitated by seeding with crystals of $N^G$-monomethyl-L-arginine hydrochloride. Alternatively, crystalline $N^G$-monomethyl-L-arginine hydrochloride can be prepared by dissolving a salt of $N^G$-monomethyl-L-arginine other than the hydrochloride salt with hydrochloric acid and removing the original salt forming ion by crystallising out the hydrochloride salt.

7 Claims, No Drawings

NG-MONOMETHYL-L-ARGININE HYDROCHLORIDE DERIVATIVES AND THEIR USE IN THE TREATMENT OF SEPTIC SHOCK

This is a division of application Ser. No. 08/862,468, filed May 23, 1997, now U.S. Pat. No. 5,767,312 which is a Continuation of Ser. No. 08/461,163, filed Jun. 5, 1995, now abandoned; which is a continuation of Ser. No. 08/374,636, filed Jan. 23, 1995, now abandoned.

The present invention relates to novel crystalline salts of (S)-N5-[imino(methyl amino)methyl]ornithine, pharmaceutical compositions containing such salts and their use in medicine, more particularly the treatment and/or prophylaxis of septic shock especially the hypotension associated therewith.

International patent application WO91/04024 (U.S. Pat. No. 5,028,627) describes the use of an $N^G$ substituted arginine or an $N^G$-$N^G$-disubstituted arginine to treat hypotension. In particular, this patent application describes the use of $N^G$-monomethyl-L-arginine (also known as (S)-$N^5$[imino(methylamino)methyl]ornithine or L-NMMA) to counteract the production of nitric oxide in induced hypotension and septic shock. Nitric oxide is a potent vasodilator and cytotoxic agent that is normally produced in the endothelium as an endogenous regulator of vascular tone and in macrophages as part of the host defence mechanism. Inappropriate increase in nitric oxide synthesis leads to exaggeration in these actions, so as to cause sustained and pronounced vasodilation, leading to hypofusion of various vital organisms. Furthermore, the substantial increase in the synthesis of nitric oxide in the number of cells leading to cytotoxicity and direct tissue damage, especially to the vascular endothelium.

Kilbourn et al (Proc. Natl. Acad. Sci. U.S.A., 87, 3629, 1990) report the reaction of the flavianate salt of LNMMA with Dowex 1(OH$^-$) and titrating the resulting free base of L-NMMA to pH 7.2 with hydrochloric acid. The hydrochloride was not isolated from solution.

We have now found that hydrochloric of L-NMMA may be obtained as a pure salt, for example in a crystalline form, which has considerable physical advantages, for example in terms of stability. Initial attempts to prepare the hydrochloride in crystalline form gave rise to an amorphous glass which did not crystallise. Crystals of the hydrochloride were unexpectedly obtained when the amorphous glass was left in the presence of ethanol for several months.

Accordingly, the present invention provides the hydrochloride salt of (S)-$N^5$[imino(methylamino)methyl]ornithine as a substantially pure salt for example in a solid form and more specifically in a crystalline form. This hydrochloride salt of L-NMMA is anhydrous and not hydroscopic.

Preferably the salt is at least 70%, more preferably at least 90% pure and most preferably greater than 95% pure.

The salt exists in at least three distinguishable isomorphic form (A, B and C) as identified by X-ray diffraction analysis and Differential Scanning Calorimetry (DSC), and the present invention is intended to include each isomorphic form individually or a mixture of two or more isomorphic forms.

Hygroscopicity studies have shown Form A to deliquesce at 65% humidity, whilst Form B is considerably less hygroscopic. DSC shows Form A to be the more thermodynamically stable. DSC has also been used to estimate the melting points of Forms A and B as 219° C. and ca.205° respectively.

The present invention also provides a process for preparing crystalline L-NMMA hydrochloride which process comprises reacting L-NMMA with hydrochloric acid and crystallising out the hydrochloride. Preferably the molar ratio of L-NMMA to acid is from 1:1 to 1:5 and, in particular, approximately 1 to 1. The reaction is suitably carried out by dissolving the L-NMMA in a solution of hydrochloric acid (preferably between 0.5 molar and 5 molar and conveniently 2 molar, at a non-extreme temperature, for example between 10° and 80° C., and conveniently at room temperature. The resulting solution is preferably evaporated (for example at a raised temperature, i.e. between 35° and 60°, under reduced pressure). The residue is then crystallised from a suitable solvent, for example by dissolving the residue in a minimum of hot ethanol, conveniently at boiling point, and water. It has been found that seeding the solution containing the hydrochloride salt of L-NMMA assists its crystallisation. Without seeding, the crystallation process may take several months.

The present invention further provides a process for producing L-NMMA hydrochloride which process comprises reacting a salt of L-NMMA other than the hydrochloride with hydrochloric acid and removing the original salt forming ion. Conveniently the reaction is carried out by dissolving the acetate salt of L-NMMA, in aqueous hydrochloric acid, at a concentration between 0.5 and 5 molar conveniently 2 molar. The solution is then evaporated (for example at an elevated temperature, i.e. between 30° and 70°, conveniently 60°, under reduced pressure) The residue is then dissolved in a suitable solvent, for example aqueous ethanol and cooled. Again, seeding the cooled solution with crystals of the hydrochloric salt of L-NMMA assists the crystallisation procedure.

Whilst it may be possible for the hydrochloride of L-NMMA to be administered as the raw chemical, it is preferable to present it as a pharmaceutical formulation. According to a further aspect, the present invention provides a pharmaceutical formulation comprising the hydrochloride of L-NMMA (the "active ingredient") together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon, for example, the condition and disorder of the recipient. The formulations may conveniently be presented in unit dosage form and may be prepared by any of the methods well known in the art of pharmacy. All methods include the step of bringing into association the active ingredient with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use or may be stored as a solution ready for injection. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a base such as gelatin and glycerin or sucrose and acacia.

Preferably the salt will be administered as a solution in water buffered to its own pKa.

Preferably unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 1 to 100 mg/kg per day and preferably 3 to 50 mg/kg per day. Doses of above 3 mg/kg per day may preferably be given in a series of smaller doses over a prolonged period, i.e. by infusion over several hours. The dose range for adult humans is generally from 70 mg to 7 g/day and preferably 200 mg to 3.5 g/day. Tablets or other forms of presentation provided in discrete units may conveniently contain an amount of compound of the invention which is effective at such dosage or as a multiple of the same, for instance, units containing 70 mg to 500 mg, usually around 100 mg to 300 mg.

The compounds of the invention are most suitably administered orally or by injection (intravenous or subcutaneous) and preferably by injection. The precise amount of compound administered to a patient will be the responsibility of the attendant physician. However the dose employed will depend on a number of factors, including the age and sex of the patient, the precise disorder being treated, and its severity. Also the route of administration may vary depending on the condition and its severity.

As mentioned hereinbefore $N^G$-monomethyl-L-arginine hydrochloride may be of use in the treatment and/or prophylaxis of septic shock. Accordingly, in a further aspect of the present invention there is provided $N^G$-monomethyl-L-arginine hydrochloride for use in the manufacture of a medicament for the treatment and/or prophylaxis of septic shock. A yet further aspect of the present invention provides a method of treatment or prophylaxis of septic shock which comprises the administration of a therapeutically effective amount of $N^G$-monomethyl-L-arginine hydrochloride.

The invention will now be described by way of example only.

EXAMPLE 1

Preparation of (S)-N5-[Imino(methylamino)methyl] ornithine hydrochloride (L-NMMA hydrochloride)

A mixture of ornithine hydrochloride (16.86 g, 100 mMol), N,S-dimethylthiouronium iodide (34.8 g, 150 mMol) and 2M aqueous sodium hydroxide (100 ml) was stirred at 100° C. for five hours. The solution was then cooled, adjusted to pH3 with 2M aqueous hydrochloric acid, and applied to a column of Dowex 50W-X8 (H+) resin (200 ml wet bed volume). The column was washed with water until the eluate was neutral and then eluted with 0.5M aqueous ammonium hydroxide; fractions of approximately 15 ml were taken and were monitored by the silica gel with visualisation by ninydrin. Fractions 26–45 were combined and evaporated at 45° C. under reduced pressure to give a colourless resin (9.5 g) which was dissolved in 2M aqueous hydrochloric acid and the resulting solution was evaporated at 50° C. under reduced pressure. The amorphous residue was treated with hot ethanol (108 ml) and the mixture was stirred vigorously, at the boiling point, during the dropwise addition of water (4 ml). The residue gradually dissolved and on seeding with a few crystals of the hydrochloride salt began to crystallise. The mixture was cooled and then stood at 4° C. for two hours to complete the crystallisation. The product was removed by filtration, washed with ethanol and dried in a vacuum dessicator to give pure L-NMMA hydrochloride (9.6 g) as an anhydrous colourless crystalline solid, homogeneous by tlc and hpic and with $^1$H nmr and mass spectrum consistent with the proposed structure.

EXAMPLE 2

Preparation of L-NMMA hydrochloride from the acetate monohydrate

L-NMMA acetate monohydrate (186 g) was dissolved in 2M aqueous hydrochloride acid (350 ml) and the solution was evaporated at 60° C. under reduced pressure. The residue was then dissolved in water (ca 150 ml) and evaporated under reduced pressure; the redissolution and evaporation process was then repeated twice. The residue was then dissolved in warm water (25 ml) with the addition of ethanol (25 ml) to aid mobility. The still warm solution was stirred, treated with ethanol (1200 ml), seeded with a few crystals and stirring was continued at room temperature for 5 hours. The mixture was kept overnight at 4° C. and the crystalline solid was filtered, washed with ethanol and dried in a vacuum desiccator to give pure L-NMMA hydrochloride (108 g) identical in all respects with the material described above.

EXAMPLE 3

A sample of amorphous hydrochloride, prepared as in Example 1 but without seeding, crystallised after standing under ethanol for about five months at 4° C.; this material was used for "seeding" the preparations of Examples 1 and 2.

Samples of seed crystals of L-NMMA hydrochloride are available, on request, from the School of Chemistry, the University of Birmingham, Birmingham B15 2TT.

I claim:

1. A sterile pharmaceutical composition for parenteral administration which comprises $N^G$-monomethyl-L-arginine hydrochloride with a pharmaceutically acceptable carrier.

2. A sterile pharmaceutical composition for parenteral administration which comprises $N^G$-monomethyl-L-arginine hydrochloride buffered to its own pKa in a pharmaceutically acceptable carrier.

3. An ampoule or vial containing a sterile aqueous solution for parenteral administration of $N^G$-monomethyl-L-arginine hydrochloride.

4. An ampoule or vial containing lyophilized $N^G$-monomethyl-L-arginine hydrochloride.

5. A method of treating septic shock comprising parenterally administering to a patient in need of same a therapeutically effective amount of a sterile pharmaceutical composition which comprises $N^G$-monomethyl-L-arginine hydrochloride in a pharmaceutically acceptable carrier.

6. The method of claim 5 in which the composition is administered by injection at a dose of 1 to 100 mg/kg per day.

7. The method of claim 6 in which the composition is administered by injection at a dose of 3 to 50 mg/kg per day.

* * * * *